US012667577B2

(12) United States Patent
Zou et al.

(10) Patent No.: US 12,667,577 B2
(45) Date of Patent: Jun. 30, 2026

(54) PHARMACEUTICAL COMPOSITION, AND APREPITANT INJECTION AND FREEZE-DRIED POWDER INJECTION

(71) Applicants: WISDOM PHARMACEUTICAL CO., LTD, Nantong (CN); WISDOM PHARMACEUTICAL CO., LTD. GUANGZHOU BRANCH, Guangzhou (CN)

(72) Inventors: Ping Zou, Nantong (CN); Yiguang Qi, Guangzhou (CN); Pan Liu, Guangzhou (CN); Bohao Rong, Guangzhou (CN)

(73) Assignees: WISDOM PHARMACEUTICAL CO., LTD, Nantong (CN); WISDOM PHARMACEUTICAL CO., LTD. GUANGZHOU BRANCH, Guangzhou (CN)

( * ) Notice: Subject to any disclaimer, the term of this patent is extended or adjusted under 35 U.S.C. 154(b) by 316 days.

(21) Appl. No.: 18/280,382

(22) PCT Filed: Dec. 8, 2022

(86) PCT No.: PCT/CN2022/137727
§ 371 (c)(1),
(2) Date: Sep. 5, 2023

(87) PCT Pub. No.: WO2023/197637
PCT Pub. Date: Oct. 19, 2023

(65) Prior Publication Data

US 2025/0025471 A1 Jan. 23, 2025

(30) Foreign Application Priority Data

Apr. 14, 2022 (CN) ......................... 202210391531.2

(51) Int. Cl.
*A61K 31/5377* (2006.01)
*A61K 9/19* (2006.01)
*A61K 9/51* (2006.01)

(52) U.S. Cl.
CPC ............ *A61K 31/5377* (2013.01); *A61K 9/19* (2013.01); *A61K 9/5123* (2013.01); *A61K 9/5138* (2013.01)

(58) Field of Classification Search
CPC .... A61K 31/5377; A61K 9/19; A61K 9/5123; A61K 9/5138
See application file for complete search history.

(56) References Cited

U.S. PATENT DOCUMENTS

| | | | | |
|---|---|---|---|---|
| 2009/0209541 | A1 | 8/2009 | Jain et al. | |
| 2015/0165045 | A1 | 6/2015 | Karavas et al. | |
| 2018/0369255 | A1 | 12/2018 | Prestrelski et al. | |
| 2020/0368159 | A1 | 11/2020 | Chen et al. | |
| 2021/0299059 | A1 * | 9/2021 | Liu ......................... | A61K 9/19 |

FOREIGN PATENT DOCUMENTS

| | | | | |
|---|---|---|---|---|
| CN | 1106390 | C | 4/2003 | |
| CN | 101732252 | B | 7/2011 | |
| CN | 103251556 | A | 8/2013 | |
| CN | 104619312 | A | 5/2015 | |
| CN | 105816425 | A | 8/2016 | |
| CN | 106265504 | A | 1/2017 | |
| CN | 104367551 | B | 6/2017 | |
| CN | 106852118 | A | 6/2017 | |
| CN | 107281100 | A * | 10/2017 | ............. A61K 47/26 |
| CN | 109394685 | A * | 3/2019 | .............. A61P 35/00 |
| CN | 110478316 | A | 11/2019 | |
| JP | 2021535094 | A | 12/2021 | |

OTHER PUBLICATIONS

Machine translation CN-107281100-A (Year: 2017).*
Povidone _ Sigma-Aldrich (Year: 2025).*
Common milling beads (zirconia and polystyrene)—Google Search (Year: 2025).*
Machine translation of CN-109394685-A (Year: 2019).*
MCE (Year: 2026).*
Polyvinylpyrrolidone-K12-250GR (Year: 2026).*
Toziopoulou, F. et al., Production of aprepitant nanocrystals by wet media milling and subsequent solidification, International Journal of Pharmaceutics, vol. 533 (2017) 324-334. doi: 10.1016/j.ijpharm.2017.02.065. Epub Feb. 28, 2017. PMID: 28257885.
PCT International Search Report for International Application No. PCT/CN2022/137727, mailed Feb. 28, 2023, 3pp.
PCT Written Opinion for International Application No. PCT/CN2022/137727, mailed Feb. 28, 2023, 6pp.

* cited by examiner

*Primary Examiner* — Robert A Wax
*Assistant Examiner* — John W Lippert, III
(74) *Attorney, Agent, or Firm* — MH2 Technology Law Group LLP

(57) ABSTRACT

Disclosed are a pharmaceutical composition, an aprepitant injection, and an aprepitant freeze-dried powder injection. The pharmaceutical composition comprises aprepitant, a primary stabilizer, and a secondary stabilizer, wherein the primary stabilizer comprises sodium deoxycholate and the secondary stabilizer comprises povidone. The aprepitant injection can be administered by injecting. The formulation uses a largely reduced amount of excipients, and is less irritative to an injection site, less prone to cause a hypersensitive reaction, and thus safer when being used by a patient. The formulation has good stability and can be stored and transported at room temperature, largely reducing production, storage, and transportation costs.

19 Claims, No Drawings

PHARMACEUTICAL COMPOSITION, AND APREPITANT INJECTION AND FREEZE-DRIED POWDER INJECTION

CROSS REFERENCE TO RELATED APPLICATIONS

This application is a National Phase of PCT Patent Application No. PCT/CN2022/137727 having International filing date of Dec. 8, 2022, which claims the benefit of priority of U.S. Chinese Patent Application No. 202210391531.2, filed Apr. 14, 2022, the contents of which are all incorporated herein by reference in their entirety.

FIELD OF THE INVENTION

The present disclosure relates to a pharmaceutical composition, and further relates to an aprepitant injection and an aprepitant freeze-dried powder injection.

BACKGROUND OF THE INVENTION

Aprepitant is an NK1 receptor antagonist developed and brought to market by MERCK. Approved by the FDA to be marketed as an oral capsule in 2003 under the brand name of Emend, it is clinically used to prevent acute and delayed nausea and vomiting associated with initial and repeat courses of highly emetogenic cancer chemotherapy (HEC) including high-dose cisplatin. Aprepitant is typically used clinically in combination with a glucocorticoid and a 5-HT3 antagonist in patients over 6 months old for: 1) acute and delayed nausea and vomiting related to initial and repeated courses of highly emetogenic chemotherapy (HEC) with, including, high-dose cisplatin; 2) nausea and vomiting related to initial and repeated courses of moderately emetogenic chemotherapy (MEC). The chemical structure of aprepitant is:

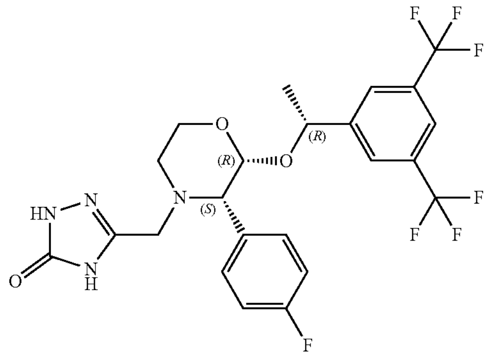

Aprepitant is a selective high-affinity antagonist of a human substance P neurokinin-1 (NK1) receptor, and has low or no affinity to a 5-hydroxytryptamine receptor 3 (5-HT3), a dopamine receptor, or a glucocorticoid receptor, the target of other existing drugs for treating chemotherapy-induced nausea and vomiting (CINV) and postoperative nausea and vomiting (PONV). Preclinical studies have shown that an NK1 receptor antagonist can inhibit vomiting caused by a cytotoxic chemotherapy drug such as cisplatin. Preclinical and human positron emission tomography (PET) studies of aprepitant show that it can penetrate the blood brain barrier to occupy an NK1 receptor in the brain. Aprepitant can inhibit acute and delayed vomiting induced by cisplatin, and enhance the antiemetic activity of ondansetron, a 5-HT3 receptor antagonist, and dexamethasone, a glucocorticoid, on cisplatin-induced vomiting.

Aprepitant is a white to off-white crystalline solid with a molecular weight of 534.43 and is insoluble in water. According to the Japanese IF document information of aprepitant capsules, at room temperature, aprepitant has a solubility of 0.00055 mg/mL in water and is slightly soluble in ethanol, isopropyl acetate, and acetonitrile. It belongs to a drug with low dissolution and low permeability, and is classified as Class IV in biopharmaceutics. Poor water solubility leads to slow and incomplete dissolution and low bioavailability of the drug. In order to improve the bioavailability of the drug, MERCK uses the nanocrystal technology to improve the bioavailability. The absolute bioavailability of the oral capsules developed by MERCK is only 60% to 65%, and it takes about 4 hours to reach a maximum concentration ($C_{max}$) of drug in blood. This is not conducive to taking effect quickly in patients before or after chemotherapy, resulting in severe limitations in clinical application scenarios.

An injection administered prior to chemotherapy has obvious clinical advantages. Its high bioavailability and rapid onset upon administration can benefit patients receiving chemotherapy for cancer to the largest extent, and further improve the drug efficacy. However, aprepitant is almost insoluble in water (0.00055 mg/mL), and is difficult to dissolve and develop into a real conventional solution injection. Poor solubility has become an obstacle for formulation researcher to overcome.

Because of the poor solubility of aprepitant, it needs to address many difficulties to develop it into an injection. After painstaking efforts, in 2010, MERCK developed aprepitant into the prodrug fosaprepitant dimeglumine to improve the solubility, and finally developed a freeze-dried powder injection, under the brand name of EMEND (fosaprepitant dimeglumine for injection). However, this prodrug injection has many defects: 1) the prodrug has poor stability and is easy to convert to aprepitant, and it is necessary to store the active pharmaceutical ingredient (hereinafter referred to as API) at −20° C.; 2) a freeze-dried fosaprepitant dimeglumine injection still has relatively poor stability, and needs to be stored at 2-8° C.; 3) the relatively poor stability of fosaprepitant dimeglumine renders the production, storage, transportation of the API and the production, transportation, and storage of formulations more expensive than ordinary injections that can be produced and stored at room temperature, resulting in higher drug costs for patients and huge waste of social medical resources; 4) the formulation of the fosaprepitant dimeglumine injection comprises a large amount of Tween 80 (58% of the amount of the active ingredient), which often causes severe pains at an injection site of the patient when being used, there being clinical data showing that an adverse effect rate (3.0%) at injection sites of fosaprepitant dimeglumine injections is higher than that of a control group (0.5%) who takes aprepitant orally; 5) fosaprepitant dimeglumine is easy to convert into aprepitant and precipitate in water, and thus has potential safety problems when being used by patients.

Heron Therapeutics Inc tried to develop aprepitant into a fat emulsion injection, and finally made it after years of efforts. In 2017, an aprepitant fat emulsion injection was approved by the FDA for being marketed under the brand name of CINVANTI with a specification of 130 mg/18 mL. The formulation comprises 2.6 g of lecithin, 0.5 g of ethanol, 0.1 g of sodium oleate, 1.7 of g soybean oil, and 1 g of sucrose. This injection still has many defects: 1) the formulation comprises large amounts of soybean oil and lecithin, the amount of excipients being 5.9 g, 45 times the amount of the active ingredient, as a result of which, a hypersensitive reaction tends to occur upon intravenous injection of the drug, harming the health of patients; 2) sodium oleate is irritant to some extent and ready to cause pains at an administration site after intravenous administration; 3) an emulsion is a thermodynamically unstable system, and this formulation still needs to be stored at 2-8° C.; 4) in addition, this formulation is of a large liquid volume, which brings about some inconveniences to clinical use and is not convenient for quick use.

In view of the defects of the products already on the market, it is still necessary to develop an injection that has a high degree of safety (less irritation at an administration site, less susceptibility to a hypersensitive reaction, etc.) and a small drug volume, is convenient to use, and can be stored and transported at room temperature, for improving patients' use safety, and meanwhile for reducing production, storage, and transportation costs, facilitating clinical use, and saving medical costs.

SUMMARY OF THE INVENTION

In view of the problems existing in the prior art, the present disclosure seeks to directly develop aprepitant into a suspension injection by using the nano-crystalline formulation technology. The development of a nano-crystalline suspension injection is difficult. Formulations that have been successfully marketed are mostly long-acting formulations in the field of psychiatric diseases. For example, the marketed drugs aripiprazole long-acting intramuscular injections and paliperidone palmitate injections are both intramuscular injection formulations. It is even more difficult to develop a nanocrystalline suspension injection that can be injected intravenously, which is limited, on the one hand, by the few types of surfactants that can be injected intravenously, and on the other hand, by the physical and chemical properties and complex formulation processes of APIs, and further by strict requirements of nanocrystalline suspension injections on particle sizes. In order to achieve the purposes of the present disclosure, the following technical solutions are adopted.

In a first aspect, the present disclosure provides a pharmaceutical composition, comprising: aprepitant, a primary stabilizer, and a secondary stabilizer, wherein the primary stabilizer comprises sodium deoxycholate and the secondary stabilizer comprises povidone. By using a combination of sodium deoxycholate and povidone as a stabilizer, the present disclosure can prepare a nanocrystalline suspension with good stability and small particle size and useful for injection.

In some embodiments, a mass ratio of the primary stabilizer to the secondary stabilizer is in the range from 1:1 to 8. In some embodiments, the mass ratio of the primary stabilizer to the secondary stabilizer is in the range from 1:(1-7), preferably in the range from 1:(2-7). In some embodiments, the mass ratio of the primary stabilizer to the secondary stabilizer is 1:1, 1:1.5, 1:2, 1:2.5, 1:3, 1:3.5, 1:4, 1:5.5, 1:6, 1:6.5, or 1:7.

In some embodiments, a mass ratio of the sodium deoxycholate to the povidone is in the range from 1:1 to 8. In some embodiments, the mass ratio of the sodium deoxycholate to the povidone is in the range from 1:(1-7), preferably in the range from 1:(2-7). The inventors have found that when the mass ratio of sodium deoxycholate to povidone is within such ranges, a nanocrystalline formulation with relatively small particle size can be prepared, and the stability of the nanocrystalline suspension can be significantly improved. In some embodiments, the mass ratio of the sodium deoxycholate to the povidone is 1:1, 1:1.5, 1:2, 1:2.5, 1:3, 1:3.5, 1:4, 1:5.5, 1:6, 1:6.5, or 1:7.

In some embodiments, a ratio of the mass of the aprepitant to the total mass of the primary stabilizer and the secondary stabilizer is in the range from 1:(0.05-3.7). In some embodiments, the ratio of the mass of the aprepitant to the total mass of the primary stabilizer and the secondary stabilizer is in the range from 1:0.1 to 2. In some embodiments, the ratio of the mass of the aprepitant to the total mass of the primary stabilizer and the secondary stabilizer is 1:0.065, 1:0.08, 1:0.1, 1:0.2, 1:0.3, 1:0.4, 1:0.5, 1:0.6, 1:0.7, 1:0.8, 1:0.9, 1:1, 1:1.1, 1:1.2, 1:1.3, 1:1.5, 1:1.6, 1:1.7, 1:1.8, 1:1.9, 1:2.0, 1:2.1, 1:2.2, 1:2.3, or 1:2.4, etc.

In some embodiments, a ratio of the mass of the aprepitant to the total mass of the sodium deoxycholate and the povidone is in the range from 1:(0.05-3.7). In some embodiments, the ratio of the mass of the aprepitant to the total mass of the sodium deoxycholate and the povidone is in the range from 1:0.1 to 2. In some embodiments, the ratio of the mass of the aprepitant to the total mass of the sodium deoxycholate and the povidone is 1:0.065, 1:0.08, 1:0.1, 1:0.2, 1:0.3, 1:0.4, 1:0.5, 1:0.6, 1:0.7, 1:0.8, 1:0.9, 1:1, 1:1.1, 1:1.2, 1:1.3, 1:1.5, 1:1.6, 1:1.7, 1:1.8, 1:1.9, 1:2.0, 1:2.1, 1:2.2, 1:2.3, or 1:2.4, etc.

In some embodiments, the povidone has a molecular weight of less than 45000, preferably less than 40000, preferably less than 35000, preferably less than 30000, preferably less than 25000, preferably less than 20000, preferably less than 15000, preferably less than 10000, preferably less than 8000, and more preferably less than 4000. In some embodiments, the povidone is one or more selected from the group consisting of povidone K30, povidone K18, povidone K17, povidone K15, and povidone K12.

In some embodiments, the primary stabilizer is sodium deoxycholate. In some other embodiments, the primary stabilizer further comprises one or two selected from the group consisting of Tween 80 and Tween 20.

In some embodiments, the secondary stabilizer is povidone.

In some embodiments, the pharmaceutical composition further comprises one or more selected from the group consisting of a pH adjuster, an osmotic pressure regulator, and a lyoprotectant. Preferably, the pH adjuster is one or more selected from the group consisting of hydrochloric acid, sodium hydroxide, citric acid, a citrate, tartaric acid, a tartrate, acetic acid, lactic acid, phosphoric acid, and a phosphate (such as sodium dihydrogen phosphate, disodium hydrogen phosphate, etc.). Preferably, the osmotic pressure regulator is one or more selected from the group consisting of sodium chloride, glucose, mannitol, and glycerin. Preferably, the lyoprotectant is one or more selected from the group consisting of sucrose, lactose, mannitol, sorbitol, polyethylene glycol, and trehalose.

In some embodiments, the pharmaceutical composition is in the form of a suspension. Preferably, the suspension has a pH value in the range from 6.0 to 8.5, in the range from 6.0 to 8.0, or in the range from 6.5 to 8.0, preferably in the range from 6.5 to 8.0, and most preferably in the range from 7.0 to 8.0. In some embodiments, the aprepitant in the suspension has a $D_{50}$ less than 200 nm, preferably less than 120 nm, preferably less than 100 nm, for example, less than 80 nm. Small particle sizes are more beneficial for product stability, and also beneficial for improving a dissolution rate.

In some embodiments, the aprepitant is in the form of a crystalline, including crystalline form I, crystalline form II (crystalline form I and crystalline form II disclosed by CN98806703.X), an amorphous form, or a mixture thereof.

In some embodiments, the pharmaceutical composition comprises or is composed of the following components: 1 part by weight of the aprepitant; 0.04-0.45 (such as 0.05, 0.06, 0.07, 0.08, 0.10, 0.15, 0.20, 0.25, 0.30, 0.35, 0.40, or 0.45) parts by weight of the primary stabilizer; 0.04-3.2 (such as 0.05, 0.06, 0.07, 0.08, 0.10, 0.15, 0.20, 0.25, 0.30, 0.35, 0.40, 0.45, 0.5, 0.55, 0.6, 0.65, 0.70, 0.75, 0.80, 0.85, 0.90, 0.95, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, or 2.9, etc.) parts by weight of the secondary stabilizer; and 0.001-0.04 (such as 0.001, 0.002, 0.003, 0.004, 0.005, 0.01, 0.012, 0.015, 0.02, or 0.03, etc.) parts by weight of the pH adjuster.

In some embodiments, the pharmaceutical composition comprises or is composed of the following components: 1 part by weight of the aprepitant; 0.04-0.45 (such as 0.05, 0.06, 0.07, 0.08, 0.10, 0.15, 0.20, 0.25, 0.30, 0.35, 0.40, 0.45) parts by weight of the primary stabilizer; 0.04-3.2 (such as 0.05, 0.06, 0.07, 0.08, 0.10, 0.15, 0.20, 0.25, 0.30, 0.35, 0.40, 0.45, 0.5, 0.55, 0.6, 0.65, 0.70, 0.75, 0.80, 0.85, 0.90, 0.95, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, or 2.9, etc.) parts by weight of the secondary stabilizer; and 0.005-0.05 (such as 0.001, 0.002, 0.003, 0.004, 0.005, 0.01, 0.012, 0.015, 0.02, 0.03, 0.04, or 0.05, etc.) parts by weight of the osmotic pressure regulator.

In some embodiments, the pharmaceutical composition comprises or is composed of the following components: 1 part by weight of the aprepitant; 0.04-0.45 parts by weight of the primary stabilizer; 0.04-3.2 parts by weight of the secondary stabilizer; 0.001-0.04 parts by weight of the pH adjuster; and 0.005-0.05 parts by weight of the osmotic pressure regulator.

In some embodiments, the pharmaceutical composition further comprises water, preferably water for injection.

In some embodiments, the pharmaceutical composition comprises or is composed of the following components: 1 part by weight of the aprepitant; 0.04-0.45 parts by weight of the primary stabilizer; 0.04-3.2 parts by weight of the secondary stabilizer; 0.001-0.04 parts by weight of the pH adjuster; 0.005-0.05 parts by weight of the osmotic pressure regulator; and water.

In some embodiments, the pharmaceutical composition comprises or is composed of the following components: 1 part by weight of the aprepitant; 0.04-0.42 parts by weight of the primary stabilizer; 0.08-2.9 parts by weight of the secondary stabilizer; 0.001-0.04 parts by weight of the pH adjuster; 0.005-0.05 parts by weight of the osmotic pressure regulator; and water.

In some embodiments, the pharmaceutical composition comprises or is composed of the following components: 1 part by weight of the aprepitant; 0.05-0.40 parts by weight of the primary stabilizer; 0.1-2.8 parts by weight of the secondary stabilizer; 0.001-0.04 parts by weight of the pH adjuster; 0.005-0.5 parts by weight of the osmotic pressure regulator; and water.

In some embodiments, the pharmaceutical composition comprises 1 part by weight of the aprepitant; 0.04-0.45 parts by weight of the sodium deoxycholate; 0.04-3.2 parts by weight of the povidone; 0.001-0.04 parts by weight of the pH adjuster; 0.005-0.05 parts by weight of the osmotic pressure regulator; and water.

In some embodiments, the pharmaceutical composition comprises 1 part by weight of the aprepitant; 0.05-0.38 parts by weight of the sodium deoxycholate; 0.1-2.00 parts by weight of the povidone; 0.001-0.04 parts by weight of the pH adjuster; and 0.005-0.05 parts by weight of the osmotic pressure regulator.

In some embodiments, the pharmaceutical composition comprises 1 part by weight of the aprepitant; 0.06-0.37 parts by weight of the sodium deoxycholate; 0.12-1.90 parts by weight of the povidone; 0.001-0.04 parts by weight of the pH adjuster; and 0.005-0.05 parts by weight of the osmotic pressure regulator.

In some embodiments, the pharmaceutical composition comprises 1 part by weight of the aprepitant; 0.06-0.35 parts by weight of the sodium deoxycholate; 0.12-1.75 parts by weight of the povidone; 0.001-0.04 parts by weight of the pH adjuster; and 0.005-0.05 parts by weight of the osmotic pressure regulator.

In a second aspect, the present disclosure provides a method of preparing a pharmaceutical composition (such as the pharmaceutical composition described in the first aspect of the present disclosure). The method of preparation comprises performing wet milling on a primary stabilizer, a secondary stabilizer, an optional component, and aprepitant, wherein the primary stabilizer comprises sodium deoxycholate; the secondary stabilizer comprises povidone; and the optional component comprises one or more selected from the group consisting of a pH adjuster and an osmotic pressure regulator.

In some embodiments, a milling medium of the wet milling is zirconia beads and/or polystyrene beads.

In some embodiments, the wet milling is performed at velocity in the range from 6.0 m/s to 17.0 m/s.

In some embodiments, the method of preparation comprises:

- step (1): dissolving the primary stabilizer and the secondary stabilizer in water for injection, followed by stirring until complete dissolution, optionally adding the pH adjuster, and adding aprepitant for homogeneous dispersion to form an initial milling suspension;
- step (2): adding a milling medium into a milling chamber, and adding the initial milling suspension into the milling chamber such as a milling cylinder to start milling at a velocity in the range from 6.0 m/s to 17.0 m/s, to obtain an aprepitant nanosuspension with a $D_{50}$ less than 200 nm; and
- step (3) filling the aprepitant nanosuspension preferably into a vial or an ampoule upon sterilization and filtration.

In a third aspect, the present disclosure provides an aprepitant injection, comprising the pharmaceutical composition described in the first aspect of the present disclosure.

The aprepitant injection provided by the present disclosure is suitable for intravenous injection. The aprepitant injection provided by the present disclosure largely reduces an amount of excipients, and has good stability.

In a fourth aspect, the present disclosure provides a freeze-dried aprepitant powder injection, comprising a freeze-dried powder prepared by freeze-drying the pharmaceutical composition described in the first aspect of the present disclosure, preferably by adding a lyoprotectant.

In some embodiments, the aprepitant accounts for 1 part by mass and the lyoprotectant accounts for 0-3.5 parts by mass. In some embodiments, the aprepitant accounts for 1 part by mass and the lyoprotectant accounts for 0.1-3, 0.15-2, 0.2-1.5, 0.2-1.0, or 0.1-0.5 parts by mass.

The present disclosure has pioneered the preparation of aprepitant into an intravenously injectable nano-crystalline suspension injection, using a largely reduced amount of excipients. The formulation as developed, when being used by a patient, is less irritant to an injection site, less prone to a hypersensitive reaction, and safer. The drug is small in volume and easy to use. The formulation has good stability and can be stored and transported at room temperature, which can greatly reduce production, storage, and transportation costs.

DETAILED DESCRIPTION OF EMBODIMENTS

In order to render the purposes, technical solutions, and advantages of the present disclosure clearer, the present disclosure will be further described in detail below in combination with examples. The specific examples described herein are only used to explain the present disclosure but not to constitute any limitation to the present disclosure.

Example 1: Effect of a Single Surfactant on a Particle Size

Different types of surfactants were used to prepare aprepitant nanosuspension injections. Proper amounts of water for injection were added into containers, into which surface stabilizers in Table 1 were added, respectively, followed by stirring until complete dissolution, and the API (aprepitant) was then added, followed by stirring until homogeneous dispersion. 0.1-0.2 mm yttrium stabilized zirconia beads that account for 80% of the volume of a milling chamber were added into a wet milling machine. Milling was performed for 3 h at a milling velocity of about 12.1-12.3 m/s. After a milling suspension was obtained, Mastersizer 3000 was used to investigate the particle size distribution. $D_{50}$ represents a particle size reaching a cumulative distribution of 50%, i.e., the volume content of particles smaller than such a size accounts for 50% of all particles. The stability of the milling suspension were preliminarily investigated (the suspensions were placed at 40° C. for 10 days to observe whether they had flocculation, aggregation or crystal growth). The results were shown in the following table 1.

TABLE 1

Suspensions particle sizes of single different surface stabilizers

| Content of active ingredient | Type and content of stabilizer | $D_{50}$ | Stability |
|---|---|---|---|
| 1 part of aprepitant | 0.3 parts of macrogol 15 hydroxystearate | 157 nm | Unstable with sample aggregation |
| 1 part of aprepitant | 0.065 parts of sodium deoxycholate | 129 nm | Unstable with sample aggregation |
| 1 part of aprepitant | 0.046 parts of poloxamer 188 | Unable to test due to too much foaming | Stability not investigated |
| 1 part of aprepitant | 0.065 parts of polysorbate 20 | 168 nm | Unstable with sample aggregation |
| 1 part of aprepitant | 0.038 parts of polysorbate 80 | 172 nm | Unstable with sample aggregation |
| 1 part of aprepitant | 0.192 parts of vitamin E polyethylene glycol succinate | 144 nm | Unstable with sample aggregation |
| 1 part of aprepitant | 0.065 parts of sodium oleate | 155 nm | Unstable with sample aggregation |

The particle size test results showed that, except poloxamer 188 contained in the formulation, other surface stabilizers all could make the average particle sizes of the nano-crystalline suspensions be less than 200 nm. Among them, the solution comprising sodium deoxycholate in the formulation had a better effect, and gave a nano-crystalline suspension having a smallest average particle size. However, there was a defect of poor stability among all the formulations. The results showed that the effects of the above single surface stabilizers for developing nano-crystalline suspension injections were poor.

Example 2: Investigation in a Combination of Two Surfactants

Two surfactants were used to prepare an aprepitant nanosuspension injection. Povidone K12, povidone K17, poloxamer 188, sodium oleate, and sodium deoxycholate were combined as surface stabilizers for milling. According to the compositions and proportions of the formulations in Table 2, proper amounts of water for injection were added into the containers, and two surface stabilizers were added in turn, followed by stirring until complete dissolution. The API (aprepitant) was then added, followed by stirring until homogeneous dispersion. 0.1-0.2 mm yttrium stabilized zirconia beads accounting for 80% of the volume of the milling chamber were added at a milling velocity of about 12.1-12.3 m/s, to obtain suspension injections to investigate particle size distributions. Mastersizer 3000 was used to investigate particle size distribution. $D_{50}$ represents a particle size reaching a cumulative distribution of 50%, i.e., the volume content of particles smaller than such a size accounts for 50% of all particles. The stability of the milling suspensions were preliminarily investigated (the suspensions were placed at 40° C. for 10 days to observe whether they had flocculation, aggregation or crystal growth). The results were shown in Table 2.

TABLE 2

Milling particle size data of different surface stabilizer combinations

| Content of active ingredient | Type and content of stabilizers | Mass ratio of primary stabilizer/secondary stabilizer | $D_{50}$ | Stability |
|---|---|---|---|---|
| 1 part of aprepitant | 0.096 parts of sodium deoxycholate, 0.3 parts of povidone K12 | 1:3.13 | 104 nm | Stable with good sample homogeneity |
| 1 part of aprepitant | 0.096 parts of sodium deoxycholate, 0.3 parts of poloxamer 188 | 1:3.13 | Unable to test due to too much foaming | Unstable with sample aggregation |
| 1 part of aprepitant | 0.065 parts of sodium deoxycholate, 0.065 parts of poloxamer 188 | 1:1 | 174 nm | Unstable with sample aggregation |
| 1 part of aprepitant | 0.065 parts of sodium deoxycholate, 0.3 parts of poloxamer 188 | 1:4.62 | Unable to test due to too much foaming | Unstable |
| 1 part of aprepitant | 0.065 parts of sodium deoxycholate, 0.065 parts of sodium oleate | 1:1 | 186 nm | Unstable with sample aggregation |
| 1 part of aprepitant | 0.065 parts of sodium deoxycholate, 0.3 parts of sodium oleate | 1:4.62 | 255 nm | Unstable with sample aggregation |
| 1 part of aprepitant | 0.065 parts of sodium deoxycholate, 0.065 parts of povidone K12 | 1:1 | 153 nm | Stable with good sample homogeneity |
| 1 part of aprepitant | 0.065 parts of sodium deoxycholate, 0.13 parts of povidone K12 | 1:2 | 131 nm | Stable with good sample homogeneity |
| 1 part of aprepitant | 0.065 parts of sodium deoxycholate, 0.3 parts of povidone K12 | 1:4.62 | 103 nm | Stable with good sample homogeneity |
| 1 part of aprepitant | 0.065 parts of sodium deoxycholate, 0.3 parts of povidone K17 | 1:4.62 | 104 nm | Stable with good sample homogeneity |
| 1 part of aprepitant | 0.131 parts of sodium deoxycholate, 0.6 parts of povidone K12 | 1:4.58 | 92 nm | Stable with good sample homogeneity |
| 1 part of aprepitant | 0.327 parts of sodium deoxycholate, 1.5 parts of povidone K12 | 1:4.59 | 106 nm | Stable with good sample homogeneity |
| 1 part of aprepitant | 0.196 parts of sodium deoxycholate, 0.9 parts of povidone K12 | 1:4.59 | 98 nm | Stable with good sample homogeneity |
| 1 part of aprepitant | 0.131 parts of sodium deoxycholate, 0.3 parts of povidone K12 | 1:2.29 | 94 nm | Stable with good sample homogeneity |
| 1 part of aprepitant | 0.131 parts of sodium deoxycholate, 1.177 parts of povidone K12 | 1:8.98 | 113 nm | Unstable with sample aggregation |
| 1 part of aprepitant | 0.131 parts of sodium deoxycholate, 0.45 parts of povidone K12 | 1:3.44 | 92 nm | Stable with good sample homogeneity |
| 1 part of aprepitant | 0.173 parts of sodium deoxycholate, 0.6 parts of povidone K12 | 1:3.47 | 93 nm | Stable with good sample homogeneity |
| 1 part of aprepitant | 0.073 parts of sodium deoxycholate, 0.6 parts of povidone K12 | 1:8.22 | 126 nm | Unstable with sample aggregation |
| 1 part of aprepitant | 0.26 parts of sodium deoxycholate, 0.9 parts of povidone K12 | 1:3.46 | 96 nm | Stable with good sample homogeneity |

The above experimental data showed that povidone K17 or povidone K12 at different concentrations could be used in combination with sodium deoxycholate to render the average particle size of the nano-crystalline suspension less than 200 nm. Surprisingly, compared with the single use of sodium deoxycholate or the combination of sodium deoxycholate with other stabilizers, the combination of sodium deoxycholate with povidone enabled a nanosuspension having a smaller $D_{50}$ (less than 150 nm, less than 120 nm, or even less than 100 nm) with good stability of solution after milling. It was further found that when the mass ratio of sodium deoxycholate to povidone was in the range from 1:(2-7), the stability of solution could be further improved. The results showed that the combination of sodium deoxycholate and povidone was suitable for the development of nano-crystalline suspension injections.

Example 3

Preparation of an Aprepitant Suspension Injection (Wet Milling Method)

Formulation (for 100 Injections):

Aprepitant: 13 g

Sodium deoxycholate: 0.85 g

Povidone K12: 3.9 g
Sodium chloride: 0.25 g
Water for injection: added to 500 mL Preparation Process:

(1) Preparation of an initial suspension: 3.9 g of povidone K12, 0.85 g of sodium deoxycholate, and 0.25 g of sodium chloride were dissolved in water for injection, followed by stirring until complete dissolution. 13 g of API aprepitant was added and dispersed homogeneously to form an initial suspension.
(2) 50 ml of yttrium stabilized milling beads (a milling medium) was added to a milling chamber, and the initial suspension was added into a milling cylinder to start milling at a velocity of 16 m/s.
(3) After 3 hours of milling, a sample was taken for tests to find the suspension to have an average particle size of less than 200 nm, thus to obtain an aprepitant nanosuspension.
(4) The nanosuspension was further diluted with the water for injection to a concentration of about 26 mg/mL, sterilized and filtered, and then filled into a sterilized vial or ampoule to prepare an aprepitant nanosuspension injection.

Example 4

Preparation of an Aprepitant Suspension Injection (Wet Milling Method)

Formulation (for 100 Injections):

Aprepitant: 13 g
Sodium deoxycholate: 1.7 g
Povidone K12: 5.85 g
Monosodium citrate or sodium dihydrogen phosphate: for adjusting the pH to be in the range from 6.5 to 7.5
Water for injection: added to 500 mL Preparation Process:

(1) Preparation of a milling suspension: 5.85 g of povidone K12 and 1.7 g of sodium deoxycholate were dissolved in the water for injection, followed by stirring until complete dissolution. Monosodium citrate or sodium dihydrogen phosphate was added to adjust the pH value of the solution to be in the range from 6.5 to 7.5. 13 g of API aprepitant was added and dispersed homogeneously to form an initial milling suspension.
(2) 50 mL of yttrium stabilized milling beads were added into a milling chamber, and the initial milling suspension was added into a milling cylinder to start milling at velocity of 16 m/s.
(3) After 3 hours of milling, a sample was taken for tests to find an average particle size of the suspension to be less than 200 nm, thus to obtain an aprepitant nanosuspension.
(4) The nanosuspension was further diluted with the water for injection to a concentration of about 26 mg/mL, sterilized and filtered, and then filled into a sterilized vial or ampoule to prepare an aprepitant nanosuspension injection.

Example 5

Preparation of Aprepitant Suspension Freeze-Dried Powder Injection (Wet Milling Method)

Formulation (for 100 Injections):

Aprepitant: 13 g
Sodium deoxycholate: 1.70 g
Povidone K12: 7.8 g
Monosodium citrate: for adjusting the pH to be in the range from 6.5 to 7.5
Mannitol: 3.9 g
Water for injection: added to 500 mL Preparation Process:

(1) Preparation of a milling suspension: 7.8 g of povidone K12, 1.70 g of sodium deoxycholate, and 3.9 g of mannitol were dissolved in the water for injection, followed by stirring until complete dissolution. Monosodium citrate was used to adjust the pH value to be in the range from 6.5 to 7.5. 13 g of API aprepitant was added and dispersed homogeneously, to form an initial milling suspension.
(2) 50 ml of yttrium stabilized milling beads were add into a milling chamber, and the initial milling suspension was add into a milling cylinder to start milling at velocity of 6 m/s.
(3) After 2 hours of milling, a sample was taken for tests to find an average particle size of the suspension to be less than 200 nm, thus to obtain an aprepitant nanosuspension.
(4) The above nanosuspension was further diluted with the water for injection to a concentration of about 26 mg/mL, sterilized, filtered, filled into a vial, and freeze-dried to obtain an aprepitant freeze-dried powder injection. The freeze-drying process was as follows:

| Stage | Set temperature | Set time | Duration | Control vacuum |
|---|---|---|---|---|
| Pre-freezing | −45° C. | 30 min | 150 min | 0 |
| First drying | −5° C. | 60 min | 670 min | 0.2 mbar |
| | 0° C. | 30 min | 90 min | 0.2 mbar |
| | 5° C. | 30 min | 240 min | 0.2 mbar |
| Second drying | 25° C. | 120 min | 240 min | 0.2 mbar |

A sample obtained upon freeze-drying appeared to be porous white blocks rather easy to re-dissolve. The particle size of a nanosuspension after re-dissolution did not change from the particle size of the nanosuspension before freeze-drying.

The suspension injection and freeze-dried powder injection prepared by the nanocrystalline technology had good stability, with the API and the finished product both capable of being stored and transported at room temperature. This could greatly reduce production, storage, and transportation costs. The API of fosaprepitant dimeglumine needs to be stored at −20° C. and the finished product thereof needs to be stored at 2-8° C. As a result, the suspension injection and freeze-dried powder injection of the present invention has relatively large advantages over fosaprepitant dimeglumine. The finished product of the aprepitant fat emulsion injection needs to be stored at 2-8° C., and thus the suspension injection and freeze-dried powder injection of the present invention is also better than the aprepitant fat emulsion injection saves storage, transportation, and use costs in the process of drug production and circulation.

The suspension injection prepared by using the nanocrystal technology comprised less excipients, the amount of which could be in the range from 0.05 to 0.35 g/injection, e.g., the amount of excipients in Example 3 was 0.05 g/injection, and that in Example 4 was 0.14 g/injection. Compared with the marketed aprepitant fat emulsion injection, the suspension injection could use a largely reduced amount of excipients. As shown in Table 3, the amount of excipients for the aprepitant fat emulsion injection is 5.9 g/injection.

TABLE 3

Formulation compositions of a marketed aprepitant fat emulsion injection (CINVANTI)

| Component | Amount (g/injection) | Effect |
|---|---|---|
| Aprepitant | 0.13 | Active ingredient |
| Egg yolk lecithin | 2.6 | Surfactant |
| Soybean oil | 1.7 | Oil phase |
| Sodium oleate | 0.1 | Surfactant |
| Ethanol | 0.5 | Cosolvent |
| Sucrose | 1 | Osmotic pressure regulator |
| Water for injection | 12 | Solvent |

Example 6: Stability Investigation Results

The stability of the aprepitant nanosuspension injection prepared in Example 3 and that of the aprepitant freeze-dried powder injection prepared in Example 5 were investigated to both have good physical and chemical stabilities.

1) Studies on the Stability of the Aprepitant Nanosuspension Injection

The stability of the aprepitant nanosuspension injection was investigated at 40° C. under acceleration for 6 months, with the data shown as follows:

| | Day 0 | Month 1 | Month 2 | Month 3 | Month 6 |
|---|---|---|---|---|---|
| Appearance | Homogeneous white emulsion suspension | Homogeneous white emulsion suspension | Homogeneous white emulsion suspension | Homogeneous white emulsion suspension | Homogeneous white emulsion suspension |
| Particle size | $D_{50}$: 92 nm | $D_{50}$: 90 nm | $D_{50}$: 93 nm | $D_{50}$: 92 nm | $D_{50}$: 96 nm |
| Particulate matter | ≥10 μm: 671.7<br>≥25 μm: 51.7 | ≥10 μm: 798.3<br>≥25 μm: 73.7 | ≥10 μm: 854.0<br>≥25 μm: 81.3 | ≥10 μm: 893.7<br>≥25 μm: 92.0 | ≥10 μm: 1185.0<br>≥25 μm: 106.7 |
| Related substance (%) | Maximum single impurity: 0.06<br>Total impurity: 0.06 | Maximum single impurity: 0.06<br>Total impurity: 0.06 | Maximum single impurity: 0.06<br>Total impurity: 0.06 | Maximum single impurity: 0.06<br>Total impurity: 0.06 | Maximum single impurity: 0.06<br>Total impurity: 0.06 |

The stability of the above aprepitant nanosuspension injection was investigated for 6 months under accelerated conditions. The results showed that none of the key quality attributes of the injection including the appearance, particle size, insoluble particle, and related substance changed, indicating that the nanosuspension injection had good stability and could be stored at room temperature.

2) The Aprepitant Nano Freeze-Dried Powder Injection

The stability of the aprepitant nano freeze-dried powder injection was investigated at 60° C. under acceleration for 5 days, 15 days, and 30 days, with the data shown as follows:

| | Day 0 | Day 5 | Day 15 | Day 30 |
|---|---|---|---|---|
| Appearance | Homogeneous white blocks | Homogeneous white blocks | Homogeneous white blocks | Homogeneous white blocks |
| Particle size | $D_{50}$: 95 nm | $D_{50}$: 97 nm | $D_{50}$: 92 nm | $D_{50}$: 97 nm |
| Particulate matter | ≥10 μm: 735.0<br>≥25 μm: 62.3 | ≥10 μm: 748.7<br>≥25 μm: 65.0 | ≥10 μm: 861.0<br>≥25 μm: 75.3 | ≥10 μm: 1185.0<br>≥25 μm: 106.7 |
| Related substance (%) | Maximum single impurity: 0.06<br>Total impurity: 0.06 | Maximum single impurity: 0.06<br>Total impurity: 0.06 | Maximum single impurity: 0.06<br>Total impurity: 0.06 | Maximum single impurity: 0.06<br>Total impurity: 0.06 |

The stability of the above aprepitant nano freeze-dried powder injection was investigated at 60° C. for 30 days. The results showed that the key quality attributes including the appearance, particle size, insoluble particles, and related substances remained unchanged, indicating that the nano injection was stable and could be stored at room temperature.

Example 7 Studies on the Effects of Different pH Adjusters on Particle Size

The effects of different pH adjusters and amounts on the particle size and stability of the nanocrystalline were investigated by testing particle sizes and properties. The pH adjuster and amount thereof were changed based on the formulation of Example 4. The test results were as follows:

| Content of active ingredient | Type and amount of pH adjuster | Property Day 0 | Property 40° C. Day 10 | $D_{50}$ Day 0 | $D_{50}$ 40° C. Day 10 |
|---|---|---|---|---|---|
| 1 part of aprepitant | 0.001 parts of monosodium citrate | Homogeneous white emulsion suspension | Homogeneous white emulsion suspension | 94 nm | 99 nm |
| 1 part of aprepitant | 0.005 parts of monosodium citrate | Homogeneous white emulsion suspension | Homogeneous white emulsion suspension | 95 nm | 98 nm |
| 1 part of aprepitant | 0.01 parts of monosodium citrate | Homogeneous white emulsion suspension | Homogeneous white emulsion suspension | 94 nm | 98 nm |
| 1 part of aprepitant | 0.03 parts of sodium dihydrogen phosphate | Homogeneous white emulsion suspension | Homogeneous white emulsion suspension | 92 nm | 97 nm |
| 1 part of aprepitant | 0.04 parts of sodium dihydrogen phosphate | Homogeneous white emulsion suspension | Homogeneous white emulsion suspension | 93 nm | 98 nm |
| 1 part of aprepitant | 0.045 parts of sodium dihydrogen phosphate | Homogeneous white emulsion suspension | Large amount of aggreation | 93 nm | 183 nm |

The experimental data showed that the average particle size of the nanocrystalline suspension could be less than 200 nm using either sodium citrate or sodium dihydrogen phosphate as the pH adjuster, with the solution after milling being in good stability. When sodium dihydrogen phosphate was added as a pH adjuster, a nanocrystalline suspension with smaller $D_{50}$ (less than 150 nm, less than 120 nm, or even less than 100 nm) could be obtained. It was further found that a weight ratio of aprepitant to the pH adjuster in the range from 1:0.001 to 0.04 could further improve the stability of the solution.

Example 8: Conclusion of Animal PK Experiments

The in vivo PK of the marketed fosaprepitant dimeglumine freeze-dried powder injection (EMEND) and that of the nanosuspension injection prepared in Example 4 were compared.

Test method: Two groups of male SD rats were used, 6 rats in each group (about 300 g in weight). Each rat was administered with 0.5 ml of drug, the fosaprepitant dimeglumine freeze-dried powder injection and the nanosuspension injection prepared in the present disclosure both being diluted to a concentration of 1 mg/mL. After administration, blood samples were taken at 2, 10, 20, 30, 40 minutes and 1, 1.5, 2, 3, 5, 12, and 18 hours, respectively, and LC-MS/MS was used to test the concentrations of total aprepitant in the blood samples. The results of animal PK studies showed that the nanosuspension injection prepared in Example 4 was equivalent to and could be equivalent substitution of the fosaprepitant dimeglumine freeze-dried powder injection in terms of PK in animals, but had smaller irritations at injection sites and thus safer for patients to use than the marketed fosaprepitant dimeglumine injection or aprepitant fat emulsion injection.

Example 9: Comparison of Vascular Irritation

A comparison was made between the marketed fosaprepitant dimeglumine freeze-dried powder injection (EMEND) and the aprepitant fat emulsion injection (CINVANTI).

A: an aprepitant suspension injection prepared in Example 3;

B: an aprepitant freeze-dried powder injection prepared in Example 5;

C: a fosaprepitant dimeglumine freeze-dried powder injection (EMEND); and

D: an aprepitant fat emulsion injection (CINVANTI).

Test method: 5 rabbits in each group, weighing 2.3-2.8 kg, were each intravenously injected with a test drug in the left ear and normal saline in the same amount in the right ear as a self control at a dose volume of 1 ml/kg (the concentration of the test drug was 1 mg/mL). Irritations at the administration sites was observed and scored 1 hour and 24 hours after administration, respectively.

After the animals were killed the next day, tissue samples (3-10 mm at a proximal end and 20-30 mm a distal end) were cut from the injection sites, fixed in 10% neutral buffered formalin (NBF), and evaluated under a microscope. The tissues used for evaluation were embedded in paraffin blocks, cut into thin slices, and stained with hematoxylin and eosin for microscopic evaluation. Histopathological evaluation was performed on all collected tissues, and the findings of loss of venous endothelial cells, inflammatory cell infiltration, and the like were evaluated.

TABLE 4

| General examination grading of vascular irritation tests | |
|---|---|
| Score | Vascular wall irritation |
| 0 | No obvious irritation |
| 1 | Mild hyperemia or erythema |
| 2 | Mild to moderate hyperemia and swelling |
| 3 | Moderate to severe congestion, swelling, and eardrop |
| 4 | The same as those of score 3, with mild to moderate necrosis |
| 5 | The same as those of score 3, with severe extensive necrosis |

TABLE 5

| Histopathology scoring table | |
|---|---|
| Histopathological phenomenon | Score |
| Loss of venous endothelial cells | |
| None | 0 |
| Less than ⅓ of vascular cross-section | 1 |
| ⅓ to ½ of vascular cross-section | 2 |
| More than ½ of vascular cross-section | 3 |
| Inflammatory cell infiltration | |
| None | 0 |
| Small number of inflammatory cells in vascular wall | 1 |
| Large number of inflammatory cells in vascular wall | 2 |
| Large number of complex and dense inflammatory cells in vascular wall | 3 |

Test Results:

1. Irritant Results of Rabbit Ear Veins

The right ear, as the control group, had no obvious reaction after the injection of normal saline; and upon injection of the test drug into the left ear, the irritant results were shown in the following table:

| | 1 h | | | | | | | | | | 24 h | | | | | | | | | |
|---|---|---|---|---|---|---|---|---|---|---|---|---|---|---|---|---|---|---|---|---|
| Group | Right ear | | | | | Left ear | | | | | Right ear | | | | | Left ear | | | | |
| A | 0 | 0 | 0 | 0 | 0 | 0 | 1 | 0 | 0 | 0 | 0 | 0 | 0 | 0 | 0 | 0 | 0 | 0 | 0 | 0 |
| B | 0 | 0 | 0 | 0 | 0 | 0 | 0 | 0 | 0 | 0 | 0 | 0 | 0 | 0 | 0 | 0 | 0 | 0 | 0 | 0 |
| C | 0 | 0 | 0 | 0 | 0 | 1 | 0 | 1 | 0 | 0 | 0 | 0 | 0 | 0 | 0 | 1 | 2 | 1 | 1 | 1 |
| D | 0 | 0 | 0 | 0 | 0 | 0 | 1 | 0 | 0 | 0 | 0 | 0 | 0 | 0 | 0 | 0 | 1 | 1 | 0 | 1 |

The above results showed that in general, groups A and B developed in the present disclosure had low irritations, and were superior to the marketed products fosaprepitant dimeglumine methylamine and aprepitant injections.

2. Results of Histopathological Examination

| Group | Score | | | | |
|---|---|---|---|---|---|
| A | 0 | 1 | 0 | 0 | 0 |
| B | 0 | 0 | 0 | 0 | 0 |
| C | 1 | 2 | 2 | 1 | 1 |
| D | 0 | 1 | 0 | 2 | 1 |

According to the above results of rabbit ear vein irritant and histopathological examinations, the nanocrystalline injections prepared by the present disclosure had lower injection site irritations and higher use safety for patients than the marketed injections.

The technical solution of the present disclosure is not limited to the above specific examples, and any technical deformation made according to the technical solution of the present disclosure falls within the scope for protection of the present disclosure.

The invention claimed is:

1. A pharmaceutical composition, comprising aprepitant, a primary stabilizer, and a secondary stabilizer, wherein the primary stabilizer is sodium deoxycholate and the secondary stabilizer is povidone, and a mass ratio of sodium deoxycholate to the povidone is in the range from 1: (1-7).

2. The pharmaceutical composition according to claim 1, wherein a mass ratio of sodium deoxycholate to the povidone is in the range from 1: (2-7); and/or a mass ratio of the aprepitant to a total of the sodium deoxycholate and the povidone is in the range from 1: (0.05-3.7).

3. The pharmaceutical composition according to claim 1, wherein the povidone has a molecular weight of less than 45000.

4. The pharmaceutical composition according to claim 1, wherein the pharmaceutical composition further comprises one or more selected from a pH adjuster and an osmotic pressure regulator.

5. The pharmaceutical composition according to claim 1, wherein the pharmaceutical composition is in the form of a suspension.

6. The pharmaceutical composition according to claim 4, comprising:

1 part by weight of the aprepitant; 0.04-0.45 parts by weight of the primary stabilizer; 0.04-3.2 parts by weight of the secondary stabilizer; 0.001-0.04 parts by weight of the pH adjuster; 0.005-0.05 parts by weight of the osmotic pressure regulator; and water.

7. The pharmaceutical composition according to claim 4, comprising:

1 part by weight of the aprepitant; 0.04-0.45 parts by weight of the sodium deoxycholate; 0.04-3.2 parts by weight of the povidone; 0.001-0.04 parts by weight of the pH adjuster; and 0.005-0.05 parts by weight of the osmotic pressure regulator; or 1 part by weight of the aprepitant; 0.05-0.38 parts by weight of the sodium deoxycholate; 0.1-2.00 parts by weight of the povidone; 0.001-0.04 parts by weight of the pH adjuster; and 0.005-0.05 parts by weight of the osmotic pressure regulator; or 1 part by weight of the aprepitant; 0.06-0.37 parts by weight of the sodium deoxycholate; 0.12-1.90 parts by weight of the povidone; 0.001-0.04 parts by weight of the pH adjuster; and 0.005-0.05 parts by weight of the osmotic pressure regulator; or 1 part by weight of the aprepitant; 0.06-0.35 parts by weight of the sodium deoxycholate;

0.12-1.75 parts by weight of the povidone; 0.001-0.04 parts by weight of the pH adjuster; and 0.005-0.05 parts by weight of the osmotic pressure regulator.

8. An aprepitant injection, comprising the pharmaceutical composition of claim 1.

9. A method of preparing the pharmaceutical composition of claim 1, comprising:

step (1): dissolving a primary stabilizer and a secondary stabilizer in water for injection, followed by stirring until complete dissolution, optionally adding a pH adjuster, and adding an aprepitant for homogeneous dispersion to form an initial suspension;

step (2): adding a milling medium into a milling chamber, and adding the initial suspension into a milling cylinder to start milling at velocity in the range from 6.0m/s to 17.0m/s, to obtain an aprepitant nanosuspension with a $D_{50}$ less than 200 nm; and step (3) filling the aprepitant nanosuspension into a vial or an ampoule upon sterilization and filtration.

10. The method of preparation according to claim 9, wherein the milling medium is zirconia beads and/or polystyrene beads.

11. An aprepitant freeze-dried powder injection, comprising a freeze-dried powder prepared by adding a lyoprotectant into the pharmaceutical composition of claim 1, followed by freeze-drying.

12. The aprepitant freeze-dried powder injection according to claim 11, wherein the lyoprotectant is one or more selected from the group consisting of sucrose, lactose, mannitol, sorbitol, polyethylene glycol, and trehalose.

13. The pharmaceutical composition according to claim 3, wherein the povidone has a molecular weight of less than 15000.

14. The pharmaceutical composition according to claim 3, wherein the povidone has a molecular weight of less than 4000.

15. The pharmaceutical composition according to claim 1, wherein the povidone is one or more selected from the group consisting of povidone K30, povidone K18, povidone K17, povidone K15, and povidone K12.

16. The pharmaceutical composition according to claim 4, wherein the pH adjuster is one or more selected from the group consisting of hydrochloric acid, sodium hydroxide, citric acid, a citrate, tartaric acid, a tartrate, acetic acid, lactic acid, phosphoric acid, and a phosphate; and the osmotic pressure regulator is one or more selected from the group consisting of sodium chloride, glucose, mannitol, and glycerin.

17. The pharmaceutical composition according to claim 5, wherein the suspension has a pH value in the range from 6.0 to 8.5; and/or the aprepitant in the suspension has a $D_{50}$ less than 200 nm.

18. The pharmaceutical composition according to claim 5, wherein the suspension has a pH value in the range from 6.5 to 8.0; and/or the aprepitant in the suspension has a $D_{50}$ less than 120 nm.

19. The pharmaceutical composition according to claim 5, wherein the suspension has a pH value in the range from 7.0 to 8.0; and/or the aprepitant in the suspension has a $D_{50}$ less than 100 nm.

* * * * *